(12) United States Patent
Iwasaki et al.

(10) Patent No.: US 11,520,168 B2
(45) Date of Patent: Dec. 6, 2022

(54) CONTACT LENS AND COMMUNICATION SYSTEM

(71) Applicants: Sony Corporation, Tokyo (JP); Sony Semiconductor Solutions Corporation, Kanagawa (JP)

(72) Inventors: Masanori Iwasaki, Kanagawa (JP); Takayuki Hirabayashi, Tokyo (JP); Naoto Yamaguchi, Tokyo (JP); Tsukasa Yoshimura, Tokyo (JP); Masakazu Yajima, Kanagawa (JP); Fumiko Shiga, Tokyo (JP)

(73) Assignees: Sony Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 312 days.

(21) Appl. No.: 16/954,008

(22) PCT Filed: Nov. 28, 2018

(86) PCT No.: PCT/JP2018/043680
§ 371 (c)(1),
(2) Date: Jun. 15, 2020

(87) PCT Pub. No.: WO2019/124000
PCT Pub. Date: Jun. 27, 2019

(65) Prior Publication Data
US 2021/0080749 A1 Mar. 18, 2021

(30) Foreign Application Priority Data
Dec. 22, 2017 (JP) .............................. JP2017-245990

(51) Int. Cl.
*G02C 7/04* (2006.01)
*G02C 11/00* (2006.01)
*H01Q 1/44* (2006.01)

(52) U.S. Cl.
CPC .............. *G02C 7/049* (2013.01); *G02C 11/10* (2013.01); *H01Q 1/44* (2013.01)

(58) Field of Classification Search
CPC . H01Q 1/44; G02C 7/049; G02C 7/04; G02C 11/10; G02C 11/00
(Continued)

(56) References Cited

U.S. PATENT DOCUMENTS 9,810,926 B2 11/2017 Sako et al.
10,690,940 B2 * 6/2020 Pugh ...................... G02C 7/083
(Continued)

FOREIGN PATENT DOCUMENTS

EP 2219266 A1 8/2010
JP 2013-122591 6/2013
(Continued)

OTHER PUBLICATIONS

International Search Report issued in International Patent Application No. PCT/JP2018/043680 dated Mar. 5, 2019 and English translation of same. 5 pages.
(Continued)

*Primary Examiner* — William R Alexander
(74) *Attorney, Agent, or Firm* — K&L Gates LLP

(57) ABSTRACT

A contact lens according to an embodiment of the present disclosure includes a lens section to be worn on an eyeball. The contact lens further includes a communication electrode, a sensor device, a controller, and a shield layer in the lens section. The controller supplies electric power to the communication electrode, and outputs a signal corresponding to information acquired by the sensor device to the communication electrode. The shield layer is provided at a position facing at least one of the sensor device, the controller, or the communication electrode.

14 Claims, 15 Drawing Sheets

(58) Field of Classification Search
USPC .................................................. 351/159.01
See application file for complete search history.

(56) References Cited

U.S. PATENT DOCUMENTS

| | | | |
|---|---|---|---|
| 11,351,447 B1* | 6/2022 | Kumar | A61H 23/02 |
| 2012/0245444 A1 | 9/2012 | Otis et al. | |
| 2014/0276481 A1* | 9/2014 | Pugh | G02C 7/04 |
| | | | 351/158 |
| 2015/0005604 A1* | 1/2015 | Biederman | G02C 7/04 |
| | | | 351/158 |
| 2015/0119748 A1 | 4/2015 | Lai | |
| 2015/0183173 A1* | 7/2015 | Linhardt | B29C 66/1122 |
| | | | 425/515 |
| 2015/0362754 A1* | 12/2015 | Etzkorn | B29D 11/00817 |
| | | | 351/159.03 |
| 2017/0255030 A1* | 9/2017 | Etzkorn | B29D 11/00125 |
| 2018/0088351 A1* | 3/2018 | Kennedy | G02C 7/083 |
| 2018/0231801 A1* | 8/2018 | Gutierrez | G02C 7/04 |
| 2018/0252944 A1* | 9/2018 | Pugh | G02C 7/083 |
| 2019/0235281 A1* | 8/2019 | Etzkorn | G02C 7/04 |
| 2019/0250432 A1* | 8/2019 | Kim | G02C 11/10 |
| 2020/0064660 A1* | 2/2020 | Langford | G02C 7/04 |
| 2022/0001134 A1* | 1/2022 | Tran | G16H 30/40 |

FOREIGN PATENT DOCUMENTS

| | | |
|---|---|---|
| JP | 201475609 A | 9/2014 |
| JP | 2016-530552 | 9/2016 |
| JP | 2016530552 A | 9/2016 |
| JP | 2017-088785 | 5/2017 |
| JP | 2017-517762 | 6/2017 |
| JP | 2017-120868 | 7/2017 |
| WO | WO2014181568 | 11/2014 |
| WO | WO2018175539 A1 | 9/2018 |
| WO | WO2019116767 A | 6/2019 |

OTHER PUBLICATIONS

Written Opinion issued in International Patent Application No. PCT/JP2018/043680 dated Mar. 5, 2019 and English translation of same. 12 pages.

* cited by examiner

[ FIG. 1 ]
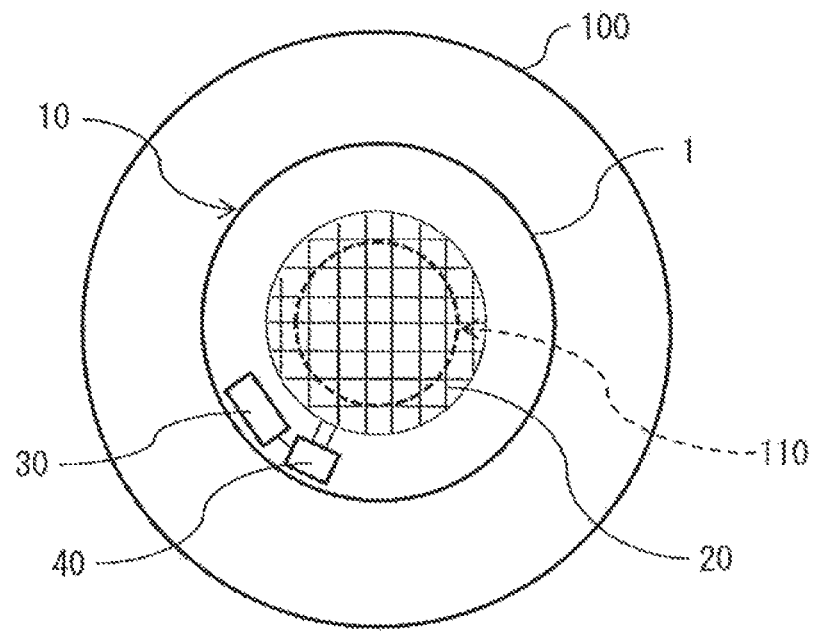
[ FIG. 2 ]
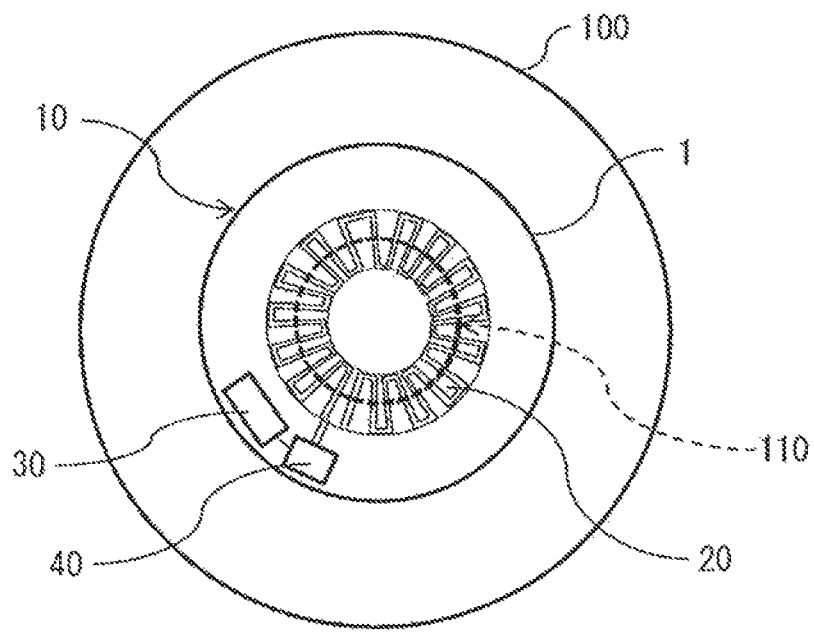

[FIG. 3]
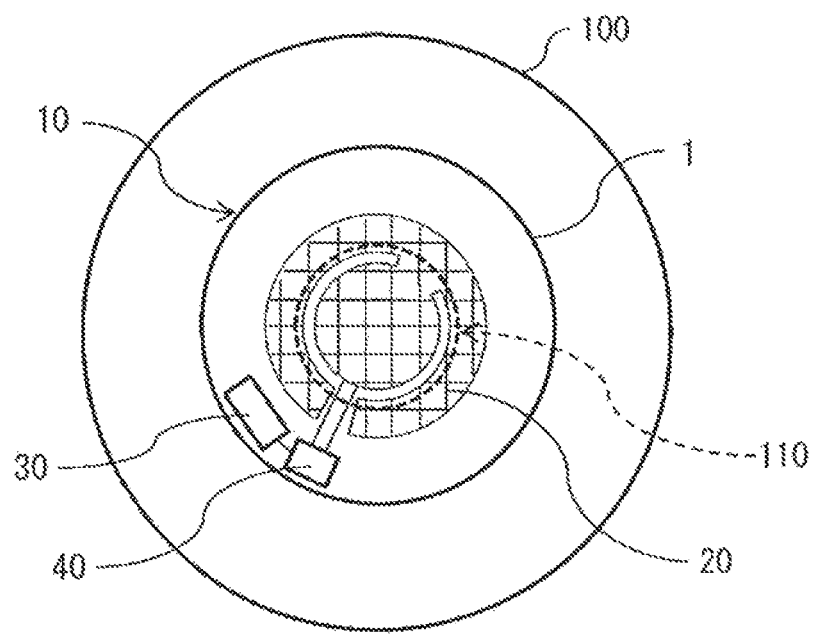
[FIG. 4]
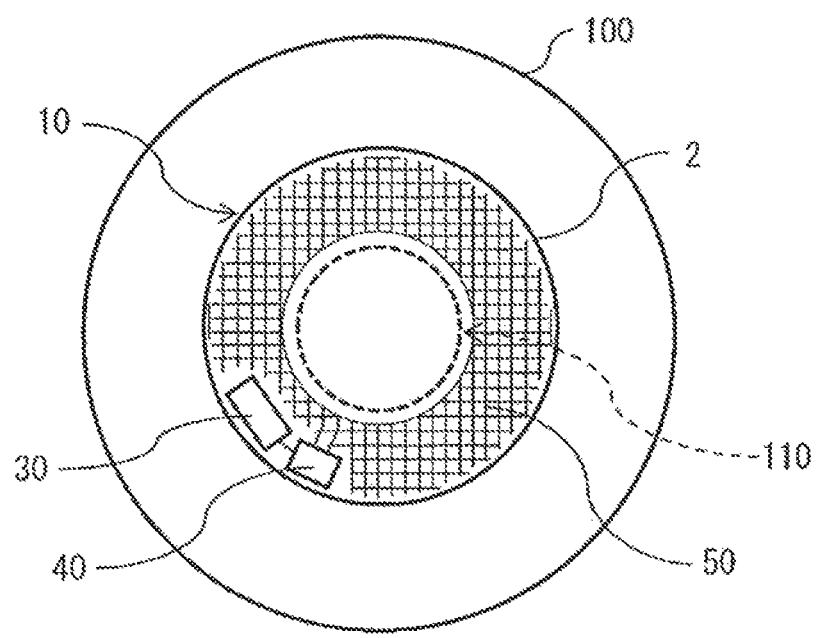

[FIG. 5]
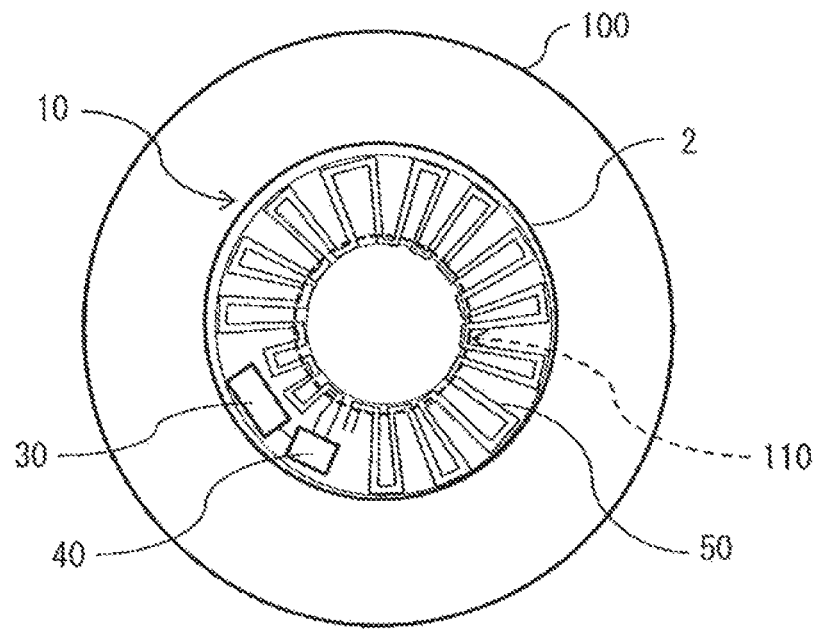
[FIG. 6]
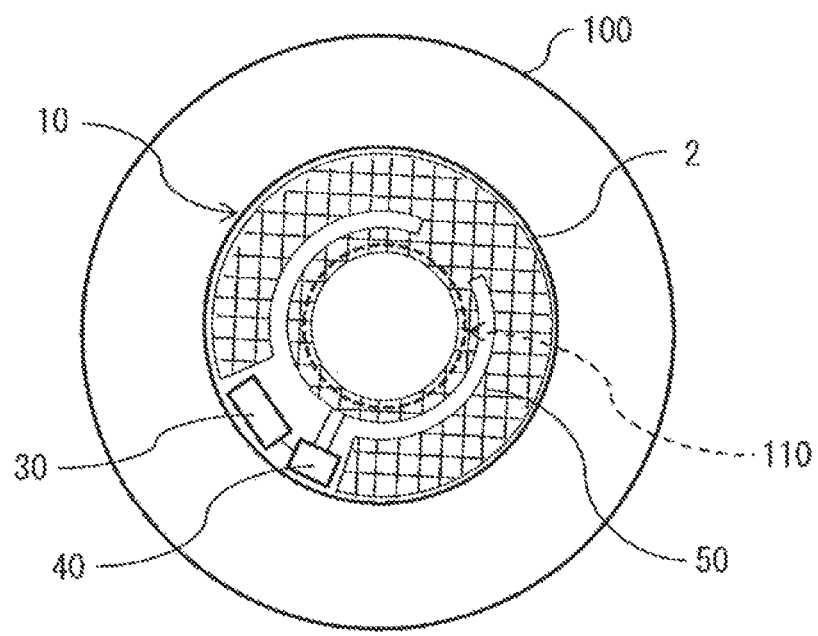

[FIG. 7]
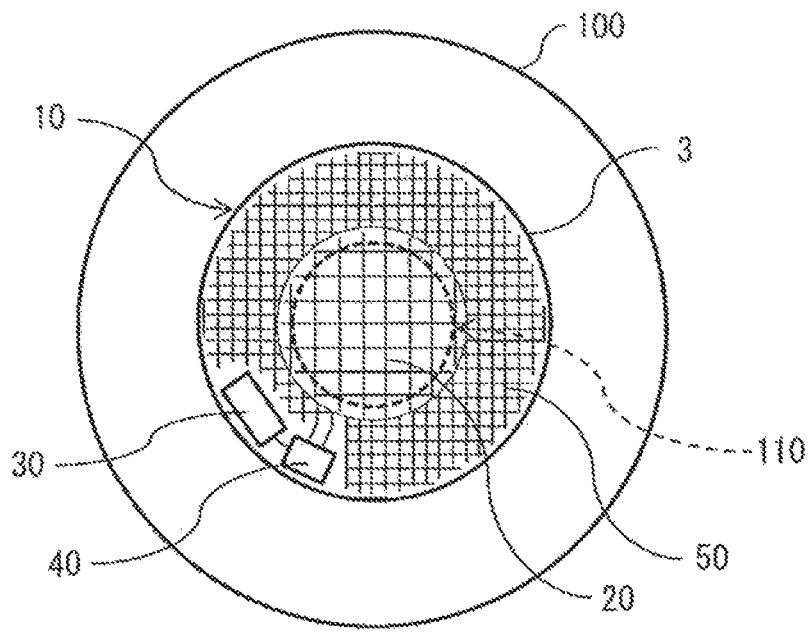
[FIG. 8]
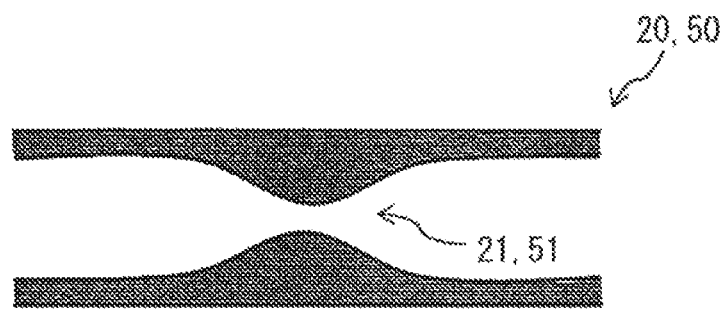
[FIG. 9]
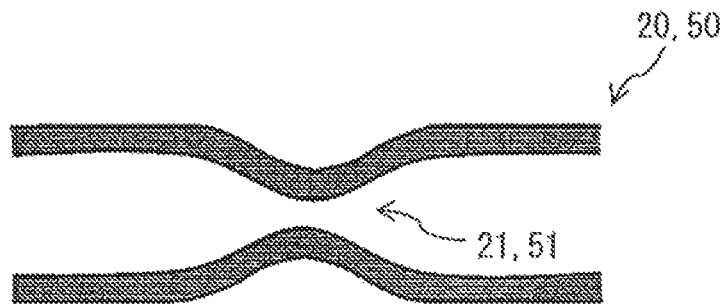

[ FIG. 10 ]
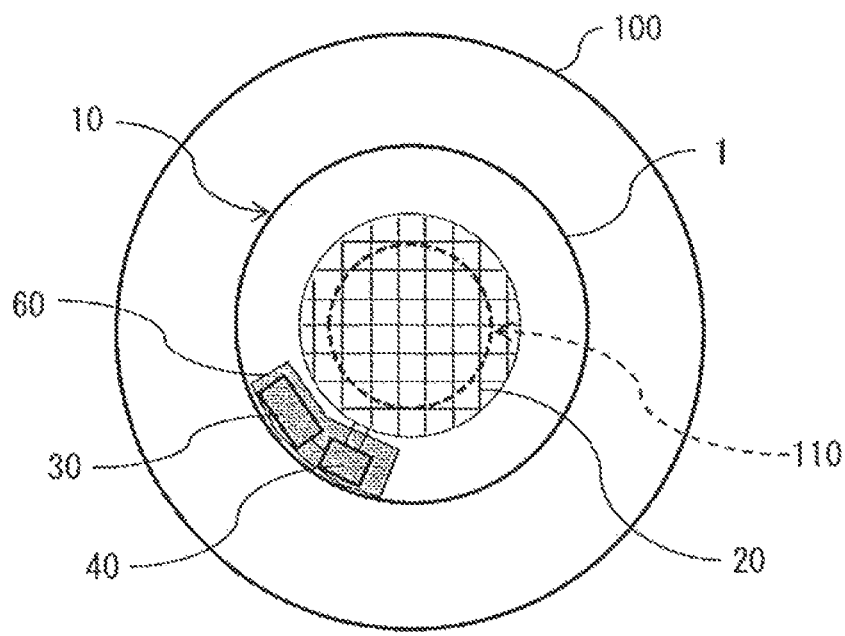
[ FIG. 11 ]
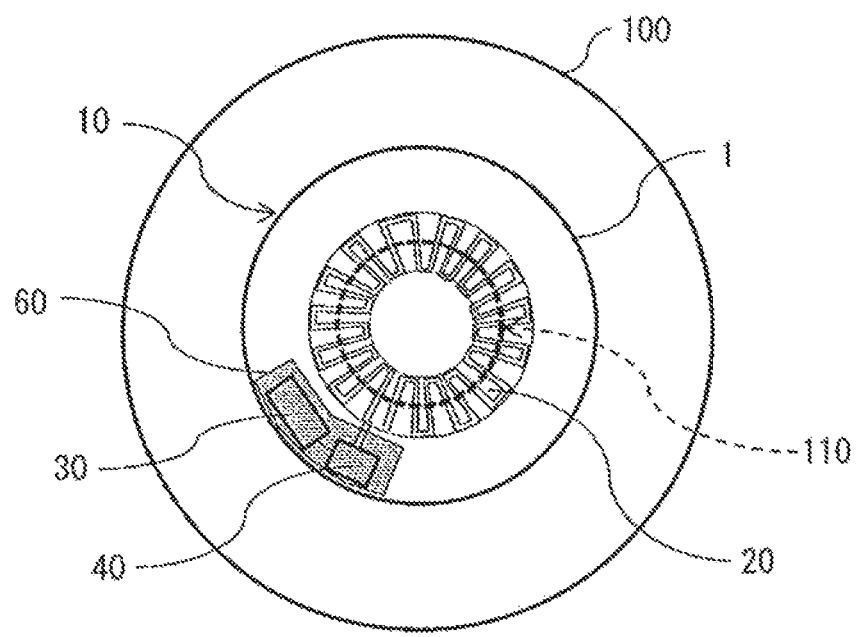

[ FIG. 12 ]
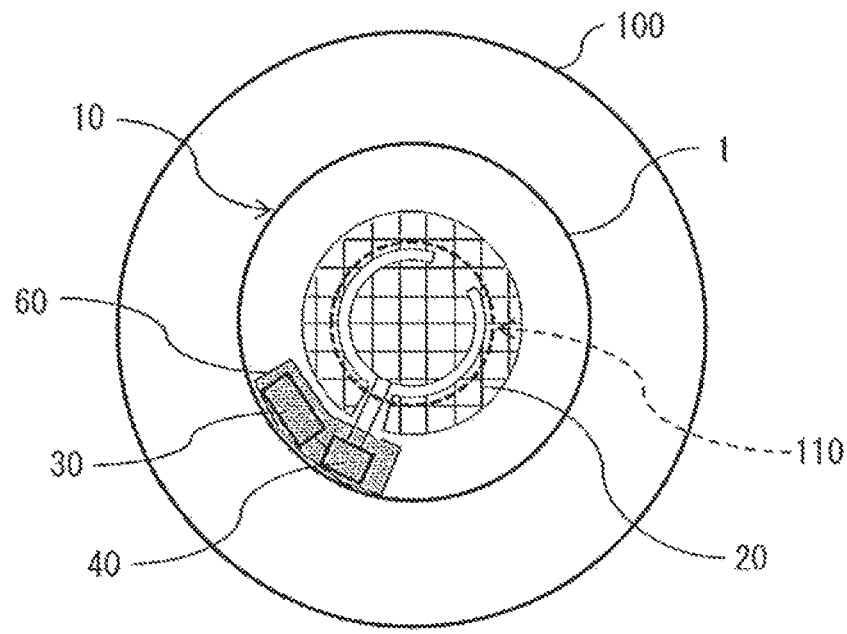
[ FIG. 13 ]
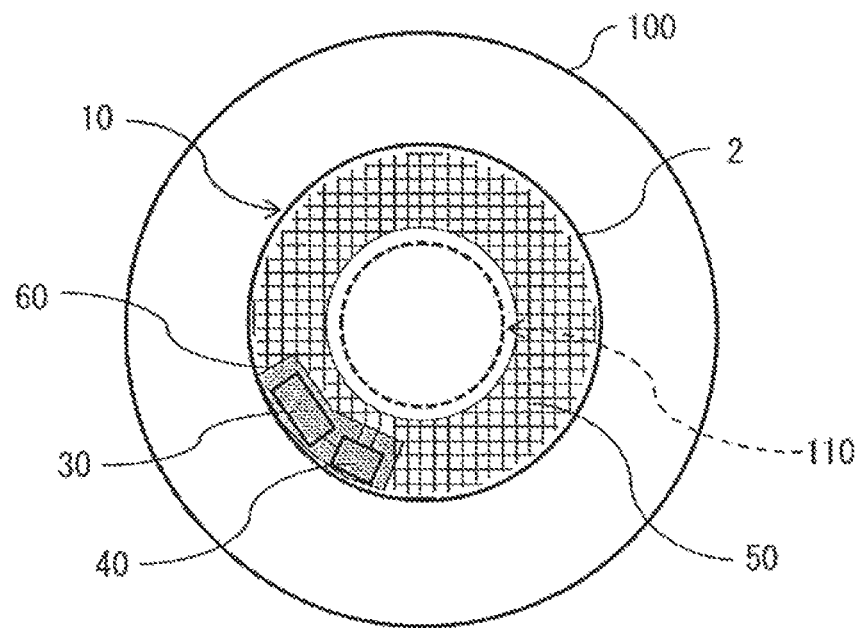

[ FIG. 14 ]
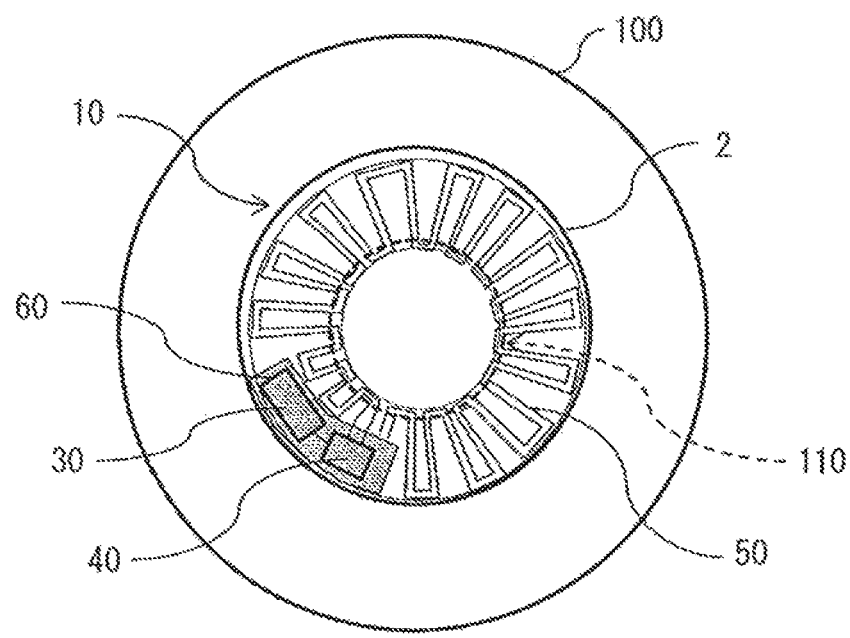
[ FIG. 15 ]
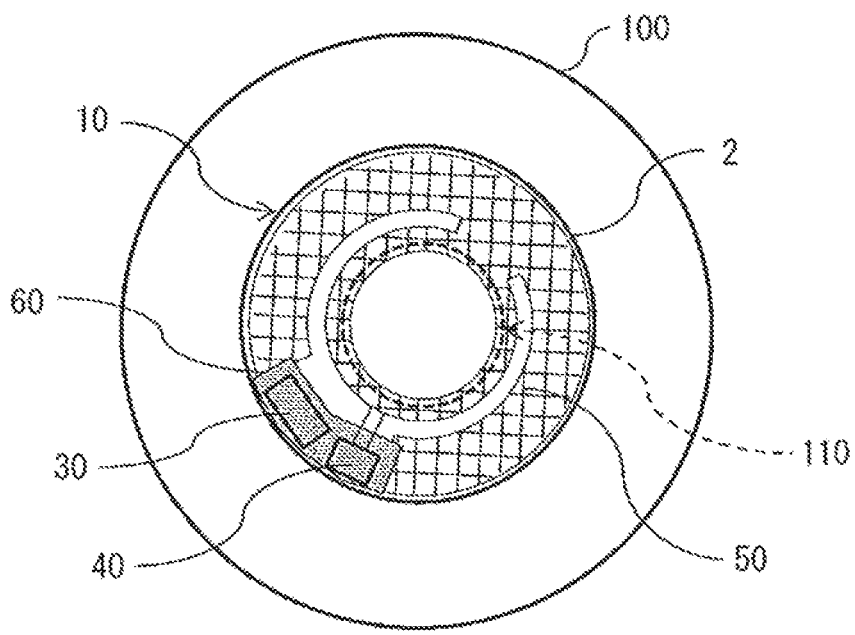

[ FIG. 16 ]
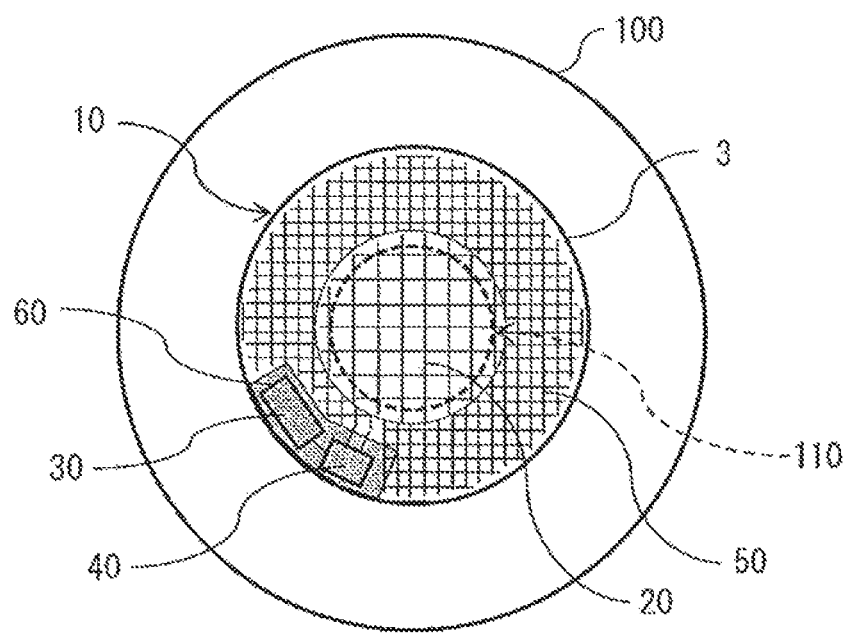
[ FIG. 17 ]
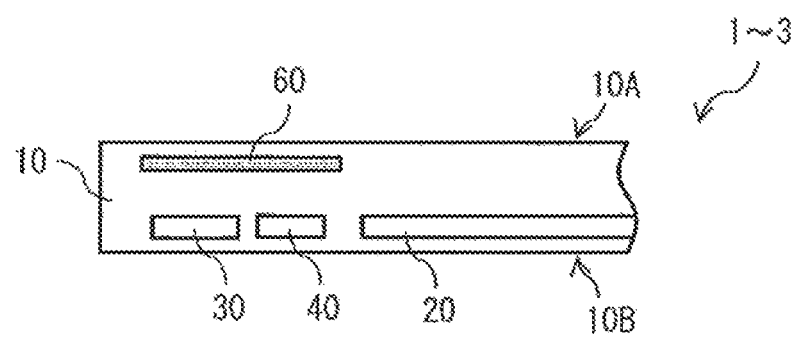

[ FIG. 18 ]
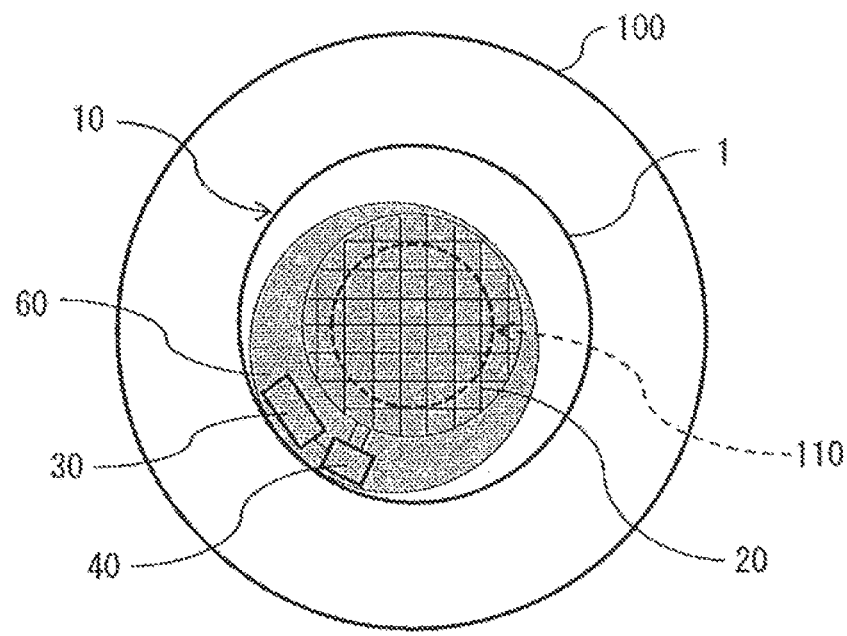
[ FIG. 19 ]
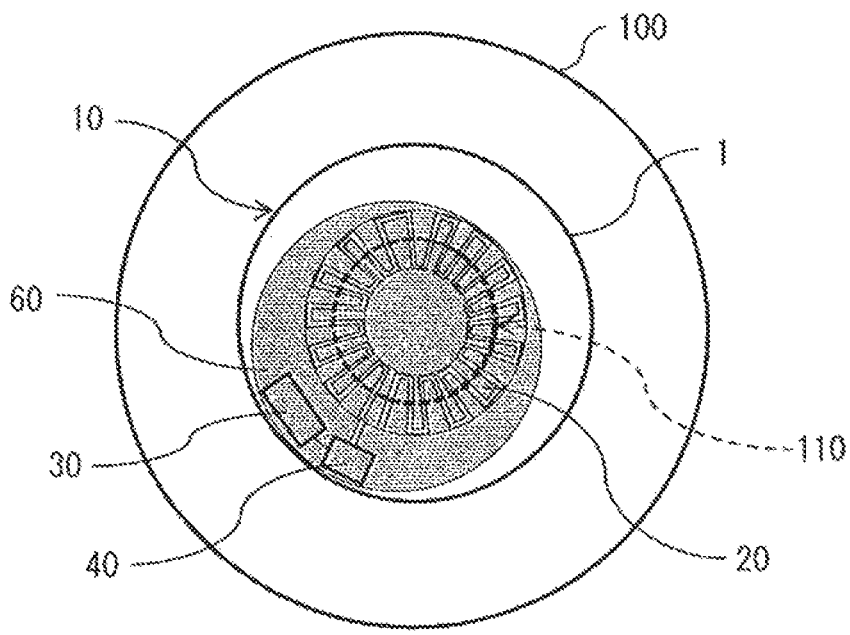

[FIG. 20]
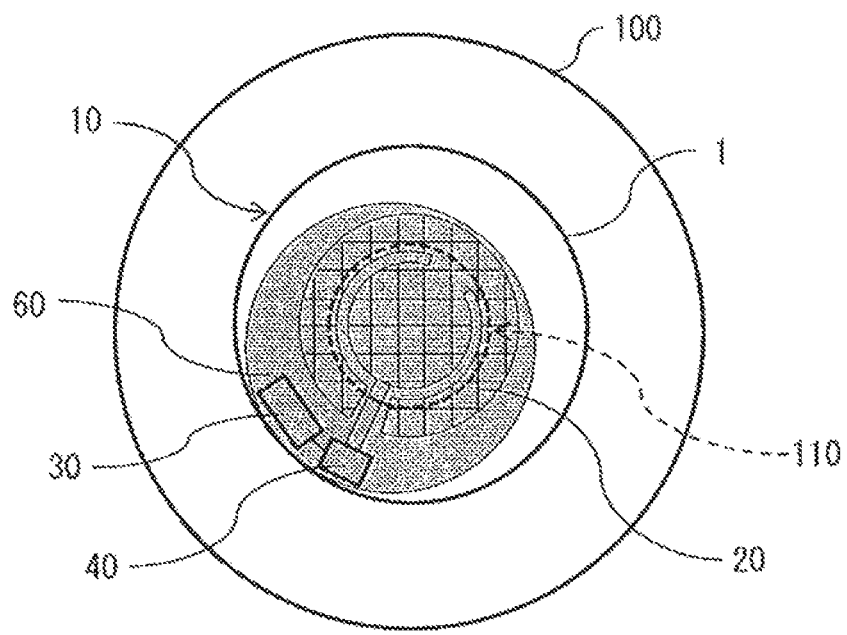
[FIG. 21]
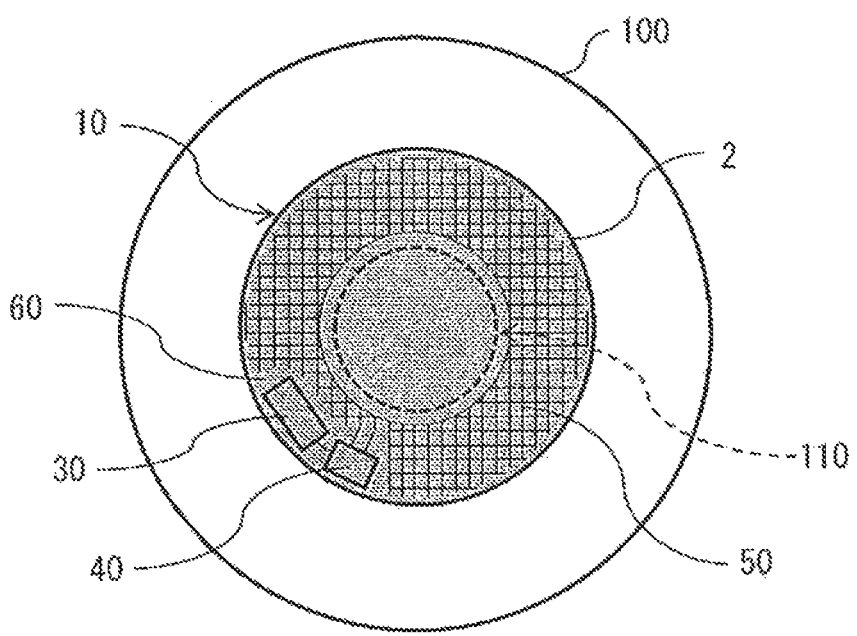

[FIG. 22]
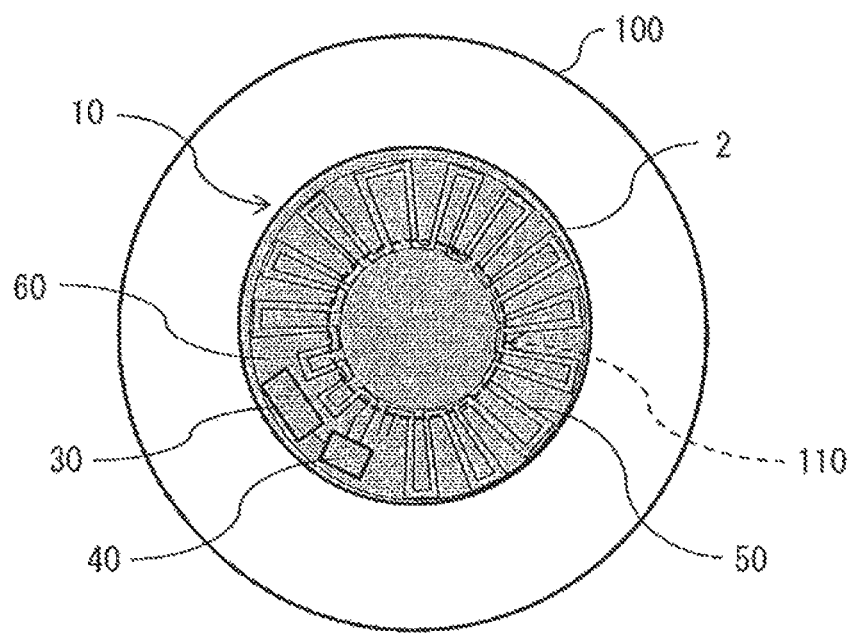
[FIG. 23]
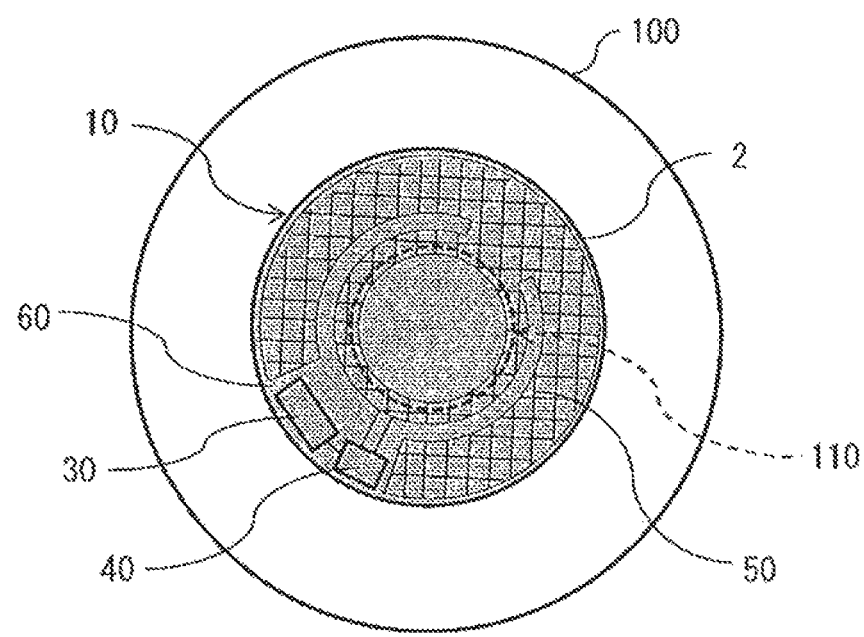

[ FIG. 24 ]
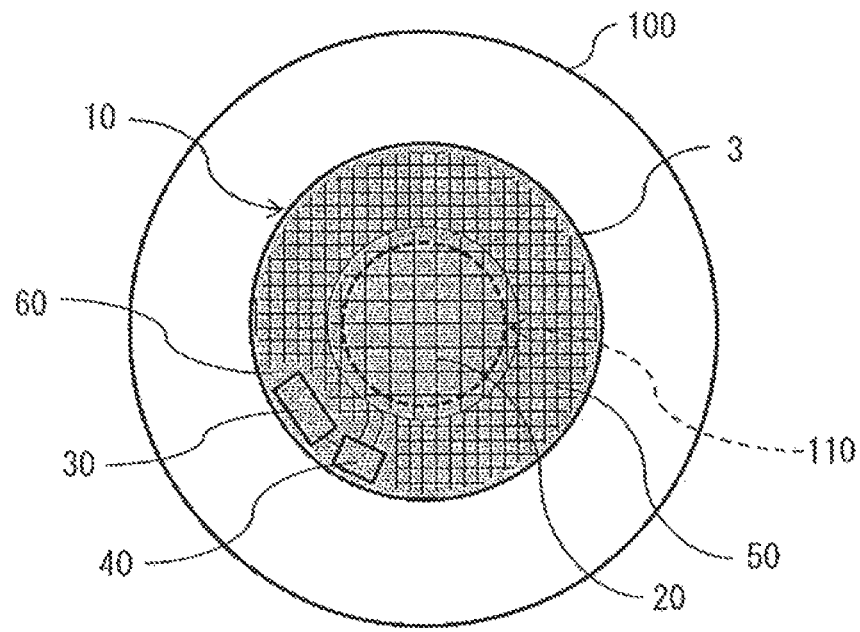
[ FIG. 25 ]
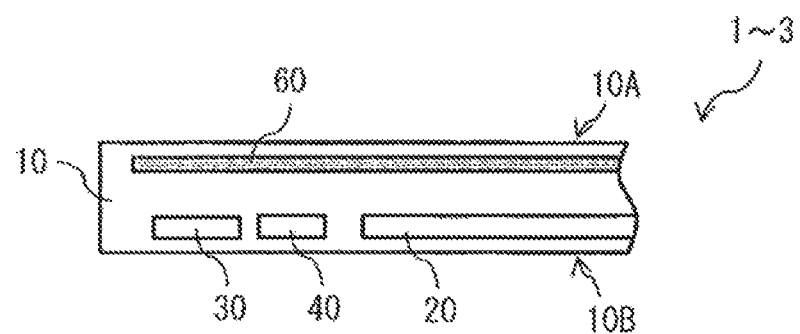
[ FIG. 26 ]
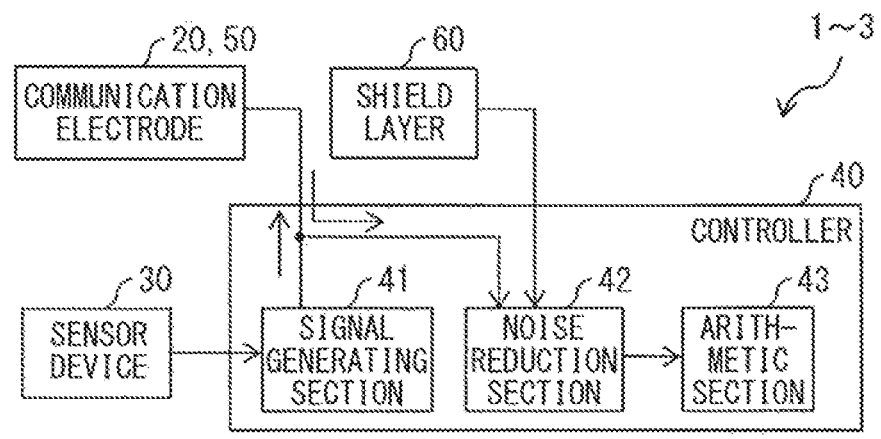

[FIG. 27]
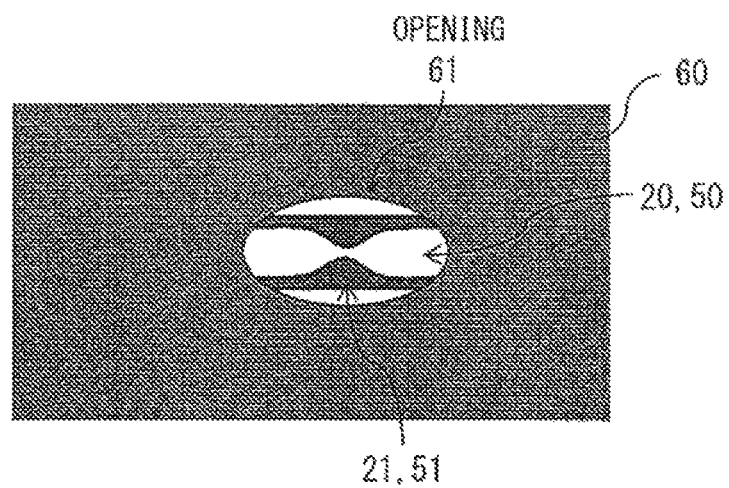
[FIG. 28]
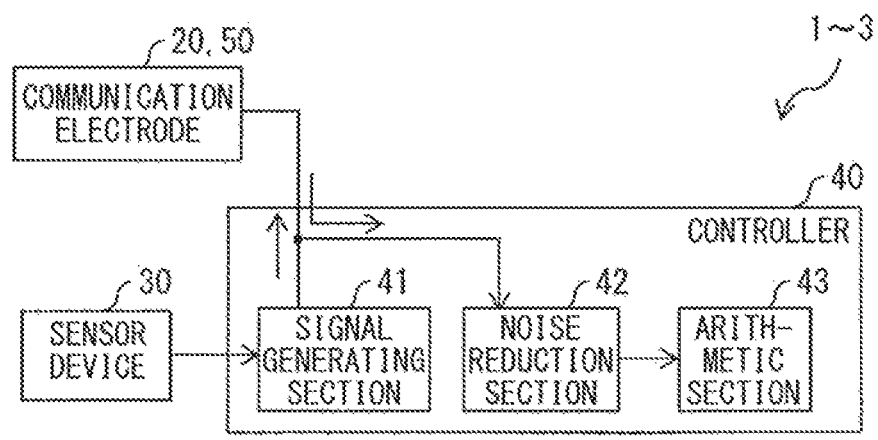

[FIG. 29]
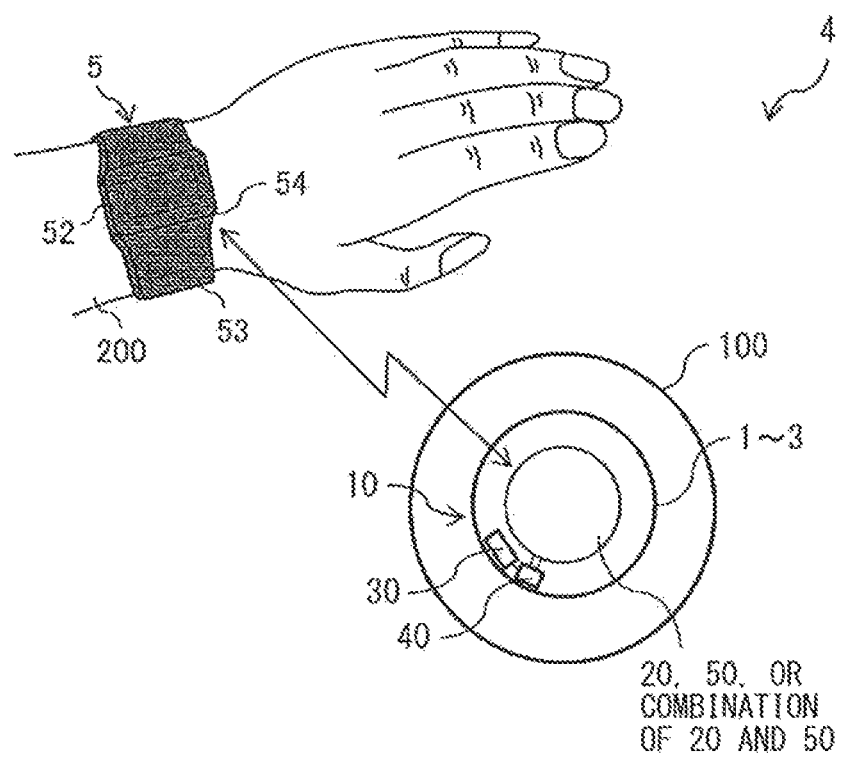

[FIG. 30]
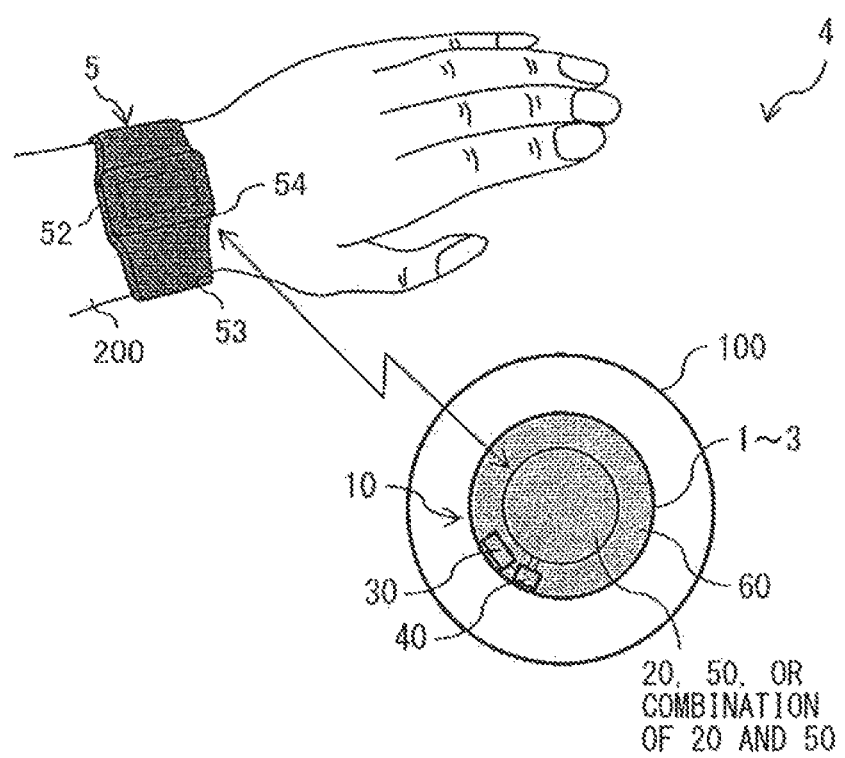

CONTACT LENS AND COMMUNICATION SYSTEM

TECHNICAL FIELD

The present disclosure relates to a contact lens and a communication system.

BACKGROUND ART

In recent years, a method has been developed that acquires biological information and the like using a contact lens.

CITATION LIST

Patent Literature

PTL 1: International Publication WO2014/181568

SUMMARY OF THE INVENTION

Incidentally, in a case where data is transmitted from a contact lens to peripheral equipment, wireless communication is typically utilized. In a case where the contact lens is worn on an eyeball, because the contact lens is small in area, and gets wet with tears, it is more likely that communication sensitivity will deteriorate, and communication speed will also degrade due to noise superimposed on a signal. Therefore, it is desirable to provide a contact lens and a communication system that exhibit enhanced noise tolerance.

A contact lens according to an embodiment of the present disclosure includes a lens section to be worn on an eyeball. The contact lens further includes a communication electrode, a sensor device, a controller, and a shield layer in the lens section. The controller supplies electric power to the communication electrode, and outputs a signal corresponding to information acquired by the sensor device to the communication electrode. The shield layer is provided at a position facing at least one of the sensor device, the controller, or the communication electrode.

A communication system according to an embodiment of the present disclosure includes a contact lens and a wearable apparatus. The contact lens includes a lens section to be worn on an eyeball. The contact lens further includes a communication electrode, a sensor device, a controller, and a shield layer in the lens section. The controller supplies electric power to the communication electrode, and outputs a signal corresponding to information acquired by the sensor device to the communication electrode. The shield layer is provided at a position facing at least one of the sensor device, the controller, or the communication electrode.

In the contact lens and the communication system according to the respective embodiments of the present disclosure, the shield layer is provided at a position facing at least one of the sensor device, the controller, or the communication electrode. This allows for reduction of an adverse influence exerted by external electric field and magnetic field, which makes it possible to perform high-accuracy measurement by the use of the sensor device.

BRIEF DESCRIPTION OF DRAWINGS

FIG. 1 is a front view of an example of a manner in which a contact lens according to a first embodiment of the present disclosure is worn on an eyeball.

FIG. 2 is a front view of a modification example of a manner in which the contact lens illustrated in FIG. 1 is worn on the eyeball.

FIG. 3 is a front view of a modification example of a manner in which the contact lens illustrated in FIG. 1 is worn on the eyeball.

FIG. 4 is a front view of a modification example of a manner in which a contact lens according to a second embodiment of the present disclosure is worn on the eyeball.

FIG. 5 is a front view of a modification example of a manner in which the contact lens illustrated in FIG. 4 is worn on the eyeball.

FIG. 6 is a front view of a modification example of a manner in which the contact lens illustrated in FIG. 4 is worn on the eyeball.

FIG. 7 is a front view of an example of a manner in which a contact lens according to a third embodiment of the present disclosure is worn on the eyeball.

FIG. 8 is a diagram of an example of a planar configuration or a cross-sectional configuration of communication electrodes illustrated in FIG. 1 to FIG. 7.

FIG. 9 is a diagram of an example of a planar configuration or a cross-sectional configuration of the communication electrodes illustrated in FIG. 1 to FIG. 7.

FIG. 10 is a front view of an example of a manner in which the contact lens in FIG. 1 or the contact lens in FIG. 1 that is provided with a communication electrode in FIG. 8 and FIG. 9 is worn on the eyeball.

FIG. 11 is a front view of an example of a manner in which the contact lens in FIG. 2 or the contact lens in FIG. 2 that is provided with the communication electrode in FIG. 8 and FIG. 9 is worn on the eyeball.

FIG. 12 is a front view of an example of a manner in which the contact lens in FIG. 3 or the contact lens in FIG. 3 that is provided with the communication electrode in FIG. 8 and FIG. 9 is worn on the eyeball.

FIG. 13 is a front view of an example of a manner in which the contact lens in FIG. 4 or the contact lens in FIG. 4 that is provided with the communication electrode in FIG. 8 and FIG. 9 is worn on the eyeball.

FIG. 14 is a front view of an example of a manner in which the contact lens in FIG. 5 or the contact lens in FIG. 5 that is provided with the communication electrode in FIG. 8 and FIG. 9 is worn on the eyeball.

FIG. 15 is a front view of an example of a manner in which the contact lens in FIG. 6 or the contact lens in FIG. 6 that is provided with the communication electrode in FIG. 8 and FIG. 9 is worn on the eyeball.

FIG. 16 is a front view of an example of a manner in which the contact lens in FIG. 7 or the contact lens in FIG. 7 that is provided with the communication electrode in FIG. 8 and FIG. 9 is worn on the eyeball.

FIG. 17 is a diagram of an example of a cross-sectional configuration of any of the contact lenses illustrated in FIG. 10 to FIG. 16.

FIG. 18 is a front view of an example of a manner in which the contact lens in FIG. 1 or the contact lens in FIG. 1 that is provided with the communication electrode in FIG. 8 and FIG. 9 is worn on the eyeball.

FIG. 19 is a front view of an example of a manner in which the contact lens in FIG. 2 or the contact lens in FIG. 2 that is provided with the communication electrode in FIG. 8 and FIG. 9 is worn on the eyeball.

FIG. 20 is a front view of an example of a manner in which the contact lens in FIG. 3 or the contact lens in FIG. 3 that is provided with the communication electrode in FIG. 8 and FIG. 9 is worn on the eyeball.

FIG. 21 is a front view of an example of a manner in which the contact lens in FIG. 4 or the contact lens in FIG. 4 that is provided with the communication electrode in FIG. 8 and FIG. 9 is worn on the eyeball.

FIG. 22 is a front view of an example of a manner in which the contact lens in FIG. 5 or the contact lens in FIG. 5 that is provided with the communication electrode in FIG. 8 and FIG. 9 is worn on the eyeball.

FIG. 23 is a front view of an example of a manner in which the contact lens in FIG. 6 or the contact lens in FIG. 6 that is provided with the communication electrode in FIG. 8 and FIG. 9 is worn on the eyeball.

FIG. 24 is a front view of an example of a manner in which the contact lens in FIG. 7 or the contact lens in FIG. 7 that is provided with the communication electrode in FIG. 8 and FIG. 9 is worn on the eyeball.

FIG. 25 is a diagram of an example of a cross-sectional configuration of any of the contact lenses illustrated in FIG. 18 to FIG. 24.

FIG. 26 is a diagram of an example of functional blocks of any of the contact lenses illustrated in FIG. 10 to FIG. 25.

FIG. 27 is a diagram of an example of any of shield layers illustrated in FIG. 10 to FIG. 25.

FIG. 28 is a diagram of an example of functional blocks of any of the contact lenses illustrated in FIG. 1 to FIG. 9.

FIG. 29 is a diagram of an example of a schematic configuration of a communication system according to a fourth embodiment of the present disclosure.

FIG. 30 is a diagram of an example of a schematic configuration of the communication system illustrated in FIG. 29.

MODES FOR CARRYING OUT THE INVENTION

Hereinafter, some embodiments of the present disclosure are described in detail with reference to the drawings. It is to be noted that descriptions are given in the following order.
1. First Embodiment
   An example where a communication electrode is provided at the middle of a lens section (FIG. 1)
2. Modification Examples of First Embodiment
   Variations of a communication electrode (FIG. 2 and FIG. 3)
3. Second Embodiment
   An example where a communication electrode is provided at an outer edge of a lens section (FIG. 4)
4. Modification Examples of Second Embodiment
   Variations of a communication electrode (FIG. 5 and FIG. 6)
5. Third Embodiment
   An example where a communication electrode is provided at each of the middle and outer edge of a lens section (FIG. 7)
6. Modification Examples in Common to Respective Embodiments
   Modification Example A: examples where a narrowed portion is provided in a communication electrode (FIG. 8 and FIG. 9)
   Modification Example B: examples where a shield layer is provided on a sensor device and a controller (FIG. 10 to FIG. 17)
   Modification Example C: examples where a shield layer is provided on a communication electrode (FIG. 18 to FIG. 25)
   Modification Example D: an example where a shield layer is used as a communication electrode for noise removal (FIG. 26)
   Modification Example E: an example where an opening is provided on a shield layer (FIG. 27)
   Modification Example F: an example where noise removal is performed without a shield layer (FIG. 28)
7. Fourth Embodiment
   Examples where communication is performed between a contact lens and a wearable apparatus (FIG. 29 and FIG. 30)

1. First Embodiment

[Configuration]

Description is provided on a contact lens 1 according to a first embodiment of the present disclosure. FIG. 1 illustrates an example of a manner in which the contact lens 1 is worn on an eyeball 100. The contact lens 1 performs near-field wireless communication (specifically, wireless communication of an electric field method or a radio wave method) with an external apparatus with a human body or a space quite close to the human body in between. The wireless communication of the electric field method refers to wireless communication using an electric field generated through an electrode. Meanwhile, the wireless communication of the radio wave method refers to wireless communication using, for example, a dipole antenna, a monopole antenna, a microstrip antenna, a patch antenna, a loop antenna, a slot antenna, or the like.

The eyeball 100 has, for example, a pupil 110. The pupil 110 contracts in bright environment, and dilates in dark environment. The contact lens 1 includes a lens section 10 to be worn on the eyeball 100, and a communication electrode 20 that is provided in the lens section 10. The contact lens 1 further includes a sensor device 30 and a controller 40.

The controller 40 supplies electric power to the communication electrode 20, and outputs a signal corresponding to information acquired by the sensor device 30 to the communication electrode 20. The controller 40 includes, for example, a processor, a storage section, and a power supply. The power supply supplies electric power to the communication electrode 20. The storage section includes, for example, a non-volatile memory, and includes, for example, an EEPROM (Electrically Erasable Programmable Read-Only Memory), a flash memory, a resistive random access memory, or the like. The storage section stores a processing program or the like to be executed by the controller 40. The processing program is a program to acquire detection data from the sensor device 30, or to output the acquired detection data to an external apparatus through the communication electrode 20. The detection data is data obtained using the contact lens 1, specifically, information detected by the sensor device 30. The processor executes, for example, the processing program stored in the storage section. The function of the processor is achieved in such a manner that the processing program is executed by the processor, for example. The processor outputs the information (the detection data) acquired by the sensor device 30 to an external apparatus through the communication electrode 20.

The sensor device 30 acquires, for example, biological information of a user who wears the contact lens 1. The sensor device 30 is a device that detects, for example, specific ingredients included in tears (for example, salt content, oxygen, lipid, blood glucose values, or hormonal substances). In this case, detection data to be acquired through detection by the sensor device 30 is information concerning the ingredients of tears. It is to be noted that the sensor device 30 may be, for example, a device that detects a line of sight, a device that detects states of blood vessels in an eyeball, a device that detects pulses of blood vessels in an eyeball, a device that detects an intraocular pressure, or a device that detects opening and closing of an eyelid. In a case where the sensor device 30 is the device that detects the line of sight, the detection data is the biological information concerning the line of sight. In a case where the sensor device 30 is the device that detects the states of the blood vessels in the eyeball, the detection data is the information concerning the blood vessels in the eyeball. In a case where the sensor device 30 is the device that detects the pulses of the blood vessels in the eyeball, the detection data is the information concerning the pulses of the blood vessels in the eyeball. In a case where the sensor device 30 is the device that detects the intraocular pressure, the detection data is the biological information concerning the intraocular pressure. In a case where the sensor device 30 is the device that detects opening and closing of the eyelid, the detection data is the biological information concerning opening and closing of the eyelid. The sensor device 30 may serve to acquire any information other than the biological information. The sensor device 30 may be, for example, a device that detects brightness of an outside, a device that detects vibration, or a device that detects temperature. In a case where the sensor device 30 is the device that detects the brightness of the outside, the detection data is the information concerning the brightness of the outside. In a case where the sensor device 30 is the device that detects the vibration, the detection data is the information concerning the vibration. In a case where the sensor device 30 is the device that detects the temperature, the detection data is the information concerning the temperature.

The lens section 10 has a curved surface shape following a surface shape of the eyeball 100. When viewed from the front, the lens section 10 takes, for example, a circular form. The lens section 10 is larger in a diameter value than a diameter of the pupil 110 at the time of dilating in the dark environment. The lens section 10 may be a lens having an eyesight correction function to correct short sightedness, long sightedness, astigmatism, etc., or may be a light transmissive base material without such an eyesight correction function. The lens section 10 includes, for example, light transmissive resin, and serves as a support base material that supports the communication electrode 20.

The communication electrode 20 is formed, for example, at the middle of the lens section 10. When the lens section 10 is worn on the eyeball 100, the communication electrode 20 is mainly provided at least in a region facing the pupil 110 at the time of contracting in the bright environment. In other words, for example, the communication electrode 20 is provided at least at a position that largely covers the region facing the pupil 110 at the time of contracting in the bright environment. The communication electrode 20 is provided, for example, inside the lens section 10.

The communication electrode 20 includes a plurality of wiring lines adjacent to each other with a predetermined gap in between. The communication electrode 20 has a mesh form as illustrated in FIG. 1, for example. The communication electrode 20 is configured using a transparent conductive wiring line that includes, for example, ITO (Indium Tin Oxide), ITiO (Indium Titanium Oxide), IZO (Indium Zinc Oxide), or carbon nanotube. It is to be noted that the communication electrode 20 may be configured using a conductive carbon wiring line or a metal wiring line. Further, the communication electrode 20 is preferably configured using a wiring line that includes, on a surface, a low-reflectance material (a material having the reflectance lower than that of a metal material) to avoid interference with a line of sight. The communication electrode 20 may be configured using a wiring line that includes a low-reflectance material (a material having the reflectance lower than that of a metal material). The communication electrode 20 may be configured using a wiring line in which at least one surface of a top surface, a side surface, or a bottom surface of a layer including a relatively higher-reflectance material is covered with a layer including a relatively lower-reflectance material. Examples of a low-reflectance material that is usable for the communication electrode 20 include carbon nanotube and the like. An aperture ratio (a ratio of a non-forming region of the communication electrode 20 that occupies a region facing the pupil 110) of the communication electrode 20 is set to maintain an optical transmittance of the contact lens 1 within an allowable range.

[Effects]

Next, description is provided on effects of the contact lens 1 according to the present embodiment.

In a case where data is transmitted from a contact lens to peripheral equipment, wireless communication is typically utilized. In a case where the contact lens is worn on an eyeball, because the contact lens is small in area, and gets wet with tears, it is more likely that communication sensitivity will deteriorate, and communication speed will also degrade. For example, in the wireless communication of the radio wave method, only formation of a thin antenna (for example, a loop antenna or the like) on an outer edge of the contact lens results in deterioration in the communication sensitivity and degradation in the communication speed. Further, for example, in the wireless communication of the electric field method, only formation of a thin antenna electrode (for example, a loop electrode or the like) on the outer edge of the contact lens results in deterioration in the communication sensitivity and degradation in the communication speed.

In contrast, in the present embodiment, the mesh-shaped communication electrode 20 is provided at a portion of the lens section 10. This makes it possible to reduce deterioration in visibility resulting from the communication electrode 20, as compared with a case where a plate-like communication electrode is provided. Further, an ability of reducing deterioration in the visibility resulting from the communication electrode 20 allows the communication electrode 20 to be provided also at the middle of the lens section 10. This makes it possible to have a wider region allowing for formation of the communication electrode 20, which makes it possible to ensure a capacity or a length of the communication electrode 20. As a result, this allows for improvement in the communication sensitivity and the communication speed.

Further, in the present embodiment, the communication electrode 20 is mainly provided in a region facing the pupil 110 when the lens section 10 is worn on the eyeball 100. This makes it possible to have a wider region allowing for formation of the communication electrode 20, which makes it possible to ensure a capacity or a length of the communication electrode 20. As a result, this allows for improvement in the communication sensitivity and the communication speed.

In addition, in the present embodiment, the communication electrode 20 is configured using the transparent conductive wiring line that includes ITO, ITiO, IZO, or carbon nanotube. This makes it possible to reduce deterioration in the visibility even in a case where the aperture ratio of the communication electrode 20 is not quite high. Further, configuration of the communication electrode 20 by the use of the transparent conductive wiring line allows the communication electrode 20 to be provided also at the middle of the lens section 10. This makes it possible to have a wider region allowing for formation of the communication electrode 20, which makes it possible to ensure a capacity or a length of the communication electrode 20. As a result, this allows for improvement in the communication sensitivity and the communication speed.

Further, in the present embodiment, electric power is supplied from the controller 40 to the communication electrode 20, and a signal corresponding to information acquired by the sensor device 30 is outputted from the controller 40 to the communication electrode 20. This allows the information acquired by the sensor device 30 to be utilized in an external apparatus.

2. Modification Examples of First Embodiment

Next, description is provided on modification examples of the contact lens 1 according to the above-described first embodiment.

Modification Example 1-1

For example, as illustrated in FIG. 2, the communication electrode 20 may take a meandering linear shape. At this time, the communication electrode 20 may include a plurality of wiring lines adjacent to each other with a narrow gap in between to ensure an increase in field intensity in the electric field communication, for example. It is to be noted that, in FIG. 2, the communication electrode 20 takes a shape in which a plurality of wiring lines meanders to surround a center of the lens section 10; however, a wiring pattern of the communication electrode 20 is not limited to a wiring pattern illustrated in FIG. 2.

In the present modification example, the communication electrode 20 takes the meandering linear shape. This makes it possible to reduce deterioration in the visibility resulting from the communication electrode 20, as compared with a case where a plate-like communication electrode is provided. Further, an ability of reducing deterioration in the visibility resulting from the communication electrode 20 allows the communication electrode 20 to be provided also at the middle of the lens section 10. This makes it possible to have a wider region allowing for formation of the communication electrode 20, which makes it possible to ensure a capacity or a length of the communication electrode 20. As a result, this allows for improvement in the communication sensitivity and the communication speed.

Modification Example 1-2

For example, as illustrated in FIG. 3, the communication electrode 20 may be a mesh-shaped slot antenna. This makes it possible to reduce deterioration in the visibility resulting from the communication electrode 20, as compared with a case where a plate-like communication electrode is provided. Further, the ability of reducing deterioration in the visibility resulting from the communication electrode 20 allows the communication electrode 20 to be provided also at the middle of the lens section 10. This makes it possible to have a wider region allowing for formation of the communication electrode 20, which makes it possible to ensure a capacity or a length of the communication electrode 20. As a result, this allows for improvement in the communication sensitivity and the communication speed.

3. Second Embodiment

[Configuration]

Next, description is provided on a contact lens 2 according to a second embodiment of the present disclosure. FIG. 4 illustrates an example of a manner in which the contact lens 2 is worn on the eyeball 100. The contact lens 1 performs near-field wireless communication (specifically, the wireless communication of the electric field method or the radio wave method) with an external apparatus with a human body or a space quite close to the human body in between. The wireless communication of the electric field method refers to wireless communication using an electric field generated through an electrode. Meanwhile, the wireless communication of the radio wave method refers to wireless communication using, for example, a dipole antenna, a monopole antenna, a microstrip antenna, a patch antenna, a loop antenna, a slot antenna, or the like.

The contact lens 2 includes a lens section 10 to be worn on the eyeball 100, and a communication electrode 50 that is provided in the lens section 10. The contact lens 2 further includes a sensor device 30 and a controller 40. The controller 40 supplies electric power to the communication electrode 50, and outputs a signal corresponding to information acquired by the sensor device 30 to the communication electrode 50. The controller 40 is configured similarly to the controller 40 according to the above-described embodiment.

The communication electrode 50 is formed, for example, on an outer edge of the lens section 10. When the lens section 10 is worn on the eyeball 100, the communication electrode 50 is mainly provided at least in a region other than a region facing the pupil 110 at the time of contracting in the bright environment. In other words, for example, the communication electrode 20 is provided at least to avoid the region facing the pupil 110 at the time of contracting in the bright environment. When the lens section 10 is worn on the eyeball 100, the communication electrode 50 may be mainly provided in a region other than a region facing the pupil 110 at the time of dilating in the dark environment. At this time, for example, the communication electrode 20 is provided to avoid the region facing the pupil 110 at the time of dilating in the dark environment. The communication electrode 50 is provided, for example, inside the lens section 10.

The communication electrode 50 includes a plurality of wiring lines adjacent to each other with a predetermined gap in between. The communication electrode 50 has a mesh form as illustrated in FIG. 4, for example. The communication electrode 50 includes a conductive carbon wiring line or a metal wiring line. It is to be noted that the communication electrode may be configured using a transparent conductive wiring line that includes ITO, ITiO, IZO, or carbon nanotube. In a case where the communication electrode 50 is not formed in a region that interferes with a field of vision, the aperture ratio (a ratio of a non-forming region of the communication electrode 20 that occupies a region which does not face the pupil 110) of the communication electrode 50 is not limited specifically. It is to be noted that, in a case where the communication electrode 50 is formed also in a region having a possibility of interfering with a field of vision, the aperture ratio is set to maintain the optical transmittance of the contact lens 2 within an allowable range.

[Effects]

Next, description is provided on effects of the contact lens 2 according to the present embodiment.

In the present embodiment, the mesh-shaped communication electrode 50 is provided at a portion of the lens section 10. This makes it possible to reduce deterioration in the visibility resulting from the communication electrode 50, as compared with a case where a plate-like communication electrode is provided. Further, the ability of reducing deterioration in the visibility resulting from the communication electrode 50 allows the communication electrode 50 to be provided also in a region having a possibility of interfering with a field of vision. This makes it possible to have a wider region allowing for formation of the communication electrode 50, which makes it possible to ensure a capacity or a length of the communication electrode 50. As a result, this allows for improvement in the communication sensitivity and the communication speed.

Further, in the present embodiment, the communication electrode 50 is mainly provided in a region that does not face the pupil 110 when the lens section 10 is worn on the eyeball 100. This makes it possible to have a wider region allowing for formation of the communication electrode 50, which makes it possible to ensure a capacity or a length of the communication electrode 50. As a result, this allows for improvement in the communication sensitivity and the communication speed.

Additionally, in the present embodiment, in a case where the communication electrode 50 includes the conductive carbon wiring line or the metal wiring line, it is possible to raise a capacity of the communication electrode 50 as compared with a case where the communication electrode 50 includes a transparent conductive material such as the ITO. As a result, this allows for improvement in the communication sensitivity and the communication speed.

Further, in the present embodiment, electric power is supplied from the controller 40 to the communication electrode 50, and a signal corresponding to information acquired by the sensor device 30 is outputted from the controller 40 to the communication electrode 50. This allows the information acquired by the sensor device 30 to be utilized in an external apparatus.

4. Modification Examples of Second Embodiment

Next, description is provided on modification examples of the contact lens 2 according to the above-described second embodiment.

Modification Example 2-1

For example, as illustrated in FIG. 5, the communication electrode 50 may take a meandering linear shape. At this time, the communication electrode 50 may include a plurality of wiring lines adjacent to each other with a narrow gap in between to ensure an increase in field intensity in the electric field communication, for example. It is to be noted that, in FIG. 5, the communication electrode 50 takes a shape in which a plurality of wiring lines meanders to surround a center of the lens section 10; however, a wiring pattern of the communication electrode 50 is not limited to a wiring pattern illustrated in FIG. 5.

In the present modification example, the communication electrode 50 takes the meandering linear shape. This makes it possible to reduce deterioration in the visibility resulting from the communication electrode 50, as compared with a case where a plate-like communication electrode is provided. Further, the ability of reducing deterioration in the visibility resulting from the communication electrode 50 allows the communication electrode 50 to be provided also in a region having a possibility of interfering with a field of vision. This makes it possible to have a wider region allowing for formation of the communication electrode 50, which makes it possible to ensure a capacity or a length of the communication electrode 50. As a result, this allows for improvement in the communication sensitivity and the communication speed.

Modification Example 2-2

For example, as illustrated in FIG. 6, the communication electrode 50 may be a mesh-shaped slot antenna. This makes it possible to reduce deterioration in the visibility resulting from the communication electrode 50, as compared with a case where a plate-like communication electrode is provided. Further, the ability of reducing deterioration in the visibility resulting from the communication electrode 50 allows the communication electrode 50 to be provided also in a region having a possibility of interfering with a field of vision. This makes it possible to have a wider region allowing for formation of the communication electrode 50, which makes it possible to ensure a capacity or a length of the communication electrode 50. As a result, this allows for improvement in the communication sensitivity and the communication speed.

5. Third Embodiment

[Configuration]

Next, description is provided on a contact lens 3 according to a third embodiment of the present disclosure. FIG. 7 illustrates an example of a manner in which the contact lens 3 is worn on the eyeball 100. The contact lens 3 performs near-field wireless communication (specifically, the wireless communication of the electric field method or the radio wave method) with an external apparatus with a human body or a space quite close to the human body in between. The wireless communication of the electric field method refers to wireless communication using an electric field generated through an electrode. Meanwhile, the wireless communication of the radio wave method refers to wireless communication using, for example, a dipole antenna, a monopole antenna, a microstrip antenna, a patch antenna, a loop antenna, a slot antenna, or the like.

The contact lens 3 includes a lens section 10 to be worn on the eyeball 100, and communication electrodes 20 and 50 that are provided in the lens section 10. The contact lens 3 further includes a sensor device 30 and a controller 40. The communication electrode 20 (a first partial electrode) is the communication electrode 20 according to the above-described first embodiment and modification examples thereof, and is mainly provided in a region facing the pupil 110 when the lens section 10 is worn on the eyeball 100. Meanwhile, the communication electrode 50 (a second partial electrode) is the communication electrode 50 according to the above-described second embodiment and modification examples thereof, and is mainly provided in a region other than the region facing the pupil 110 when the lens section 10 is worn on the eyeball 100. In the present embodiment, the aperture ratio of the communication electrode 20 is greater than the aperture ratio of the communication electrode 50, for example. It is to be noted that the aperture ratio of the communication electrode 20 may be equal to the aperture ratio of the communication electrode 50.

[Effects]

Next, description is provided on effects of the contact lens 3 of the present embodiment.

In the present embodiment, the communication electrode 20 according to the above-described first embodiment and modification examples thereof, and the communication electrode 50 according to the above-described second embodiment and modification examples thereof are provided in the lens section 10. This makes it possible to reduce deterioration in the visibility resulting from the communication electrodes 20 and 50, as compared with a case where a plate-like communication electrode is provided. Further, the ability of reducing deterioration in the visibility resulting from the communication electrodes 20 and 50 allows the communication electrodes 20 and 50 to be provided also in a region having a possibility of interfering with a field of vision. This makes it possible to have a wider region allowing for formation of the communication electrodes 20 and 50, which makes it possible to ensure a capacity or a length of each of the communication electrodes 20 and 50. As a result, this allows for improvement in the communication sensitivity and the communication speed.

6. Modification Examples in Common to Respective Embodiments

Next, description is provided on modification examples in common to the respective embodiments.

Modification Example A

Each of FIG. 8 and FIG. 9 illustrates an example of a planar configuration or a cross-sectional configuration of the communication electrodes 20 and 50 according to the above-described respective embodiments and modification examples thereof. In the above-described respective embodiments and modification examples thereof, the communication electrodes 20 and 50 each include a plurality of wiring lines adjacent to each other with a predetermined gap in between. At this time, the plurality of wiring lines configuring the communication electrode 20 has a narrowed portion 21 in which a gap narrows locally. The plurality of wiring lines configuring the communication electrode 50 has a narrowed portion 51 in which a gap narrows locally. In the narrowed portions 21 and 51, for example, as illustrated in FIG. 8, a wiring line width gets thick locally. In the narrowed portions 21 and 51, for example, as illustrated in FIG. 9, a wiring line may meander locally toward the adjacent wiring line side. In a case where a gap is narrow locally as described above, field intensity increases locally in the narrowed portion 51. As a result, an electric field generated in the narrowed portion 51 propagates farther than an electric field generated in any location other than the narrowed portion 51 in the communication electrodes 20 and 50.

In the present modification example, the narrowed portion 51 is provided in the communication electrodes 20 and 50. As a result, the electric field generated in the narrowed portion 51 propagates farther than the electric field generated in any location other than the narrowed portion 51 in the communication electrodes 20 and 50, which makes it possible to extend a distance allowing for communication between any of the contact lenses 1 to 3 and an external apparatus. Further, an intensity of the electric field generated in the narrowed portion 51 is greater than an intensity of the electric field generated in location other than the narrowed portion 51 in the communication electrodes 20 and 50, which allows for stabilization of the communication between any of the contact lenses 1 to 3 and the external apparatus.

Modification Example B

Each of FIG. 10 to FIG. 17 illustrates a modification example of any of the contact lenses 1 to 3 according to the above-described respective embodiments and modification examples thereof. FIG. 10 illustrates an example of a manner in which the contact lens 1 in FIG. 1 or the contact lens 1 in FIG. 1 that is provided with the communication electrode 20 in FIG. 8 and FIG. 9 is worn on the eyeball. FIG. 11 illustrates an example of a manner in which the contact lens 1 in FIG. 2 or the contact lens 1 in FIG. 2 that is provided with the communication electrode 20 in FIG. 8 and FIG. 9 is worn on the eyeball. FIG. 12 illustrates an example of a manner in which the contact lens 1 in FIG. 3 or the contact lens 1 in FIG. 3 that is provided with the communication electrode 20 in FIG. 8 and FIG. 9 is worn on the eyeball. FIG. 13 illustrates an example of a manner in which the contact lens 2 in FIG. 4 or the contact lens 2 in FIG. 4 that is provided with the communication electrode 20 in FIG. 8 and FIG. 9 is worn on the eyeball. FIG. 14 illustrates an example of a manner in which the contact lens 2 in FIG. 5 or the contact lens 2 in FIG. 5 that is provided with the communication electrode 20 in FIG. 8 and FIG. 9 is worn on the eyeball. FIG. 15 illustrates an example of a manner in which the contact lens 2 in FIG. 6 or the contact lens 2 in FIG. 6 that is provided with the communication electrode 20 in FIG. 8 and FIG. 9 is worn on the eyeball. FIG. 16 illustrates an example of a manner in which the contact lens 3 in FIG. 7 or the contact lens 3 in FIG. 7 that is provided with the communication electrode 20 in FIG. 8 and FIG. 9 is worn on the eyeball. FIG. 17 illustrates an example of a cross-sectional configuration of any of the contact lenses 1 to 3 in FIG. 10 to FIG. 16.

In the above-described respective embodiments and modification examples thereof, any of the contact lenses 1 to 3 may further include a shield layer 60 that prevents any entry of external electric field or magnetic field. In the present modification example, the shield layer 60 is provided at a position that faces at least one of the sensor device 30 or the controller 40, and that is located on the opposite side to the eyeball 100 in a positional relationship with the sensor device 30 and the controller 40. For example, as illustrated in FIG. 10 to FIG. 17, the shield layer 60 is mainly provided in a region other than a region facing the pupil 110 when the lens section 10 is worn on the eyeball 100. The shield layer 60 is provided, for example, inside the lens section 10. The shield layer 60 includes a conductive material. For example, the shield layer 60 includes a conductive carbon or a metal. It is to be noted that the shield layer 60 may include a transparent conductive material, such as ITO, ITiO, IZO, or carbon nanotube.

In the present modification example, the shield layer 60 is provided. This allows the sensor device 30 and the controller 40 to reduce an adverse influence exerted by the external electric field or magnetic field. This makes it possible to perform high-accuracy measurement by the use of the sensor device 30.

Modification Example C

Each of FIG. 18 to FIG. 25 illustrates a modification example of any of the contact lenses 1 to 3 according to the above-described respective embodiments and modification examples thereof. FIG. 18 illustrates an example of a manner in which the contact lens 1 in FIG. 1 or the contact lens 1 in FIG. 1 that is provided with the communication electrode 20 in FIG. 8 and FIG. 9 is worn on the eyeball. FIG. 19 illustrates an example of a manner in which the contact lens 1 in FIG. 2 or the contact lens 1 in FIG. 2 that is provided with the communication electrode 20 in FIG. 8 and FIG. 9 is worn on the eyeball. FIG. 20 illustrates an example of a manner in which the contact lens 1 in FIG. 3 or the contact lens 1 in FIG. 3 that is provided with the communication electrode 20 in FIG. 8 and FIG. 9 is worn on the eyeball. FIG. 21 illustrates an example of a manner in which the contact lens 2 in FIG. 4 or the contact lens 2 in FIG. 4 that is provided with the communication electrode 20 in FIG. 8 and FIG. 9 is worn on the eyeball. FIG. 22 illustrates an example of a manner in which the contact lens 2 in FIG. 5 or the contact lens 2 in FIG. 5 that is provided with the communication electrode 20 in FIG. 8 and FIG. 9 is worn on the eyeball. FIG. 23 illustrates an example of a manner in which the contact lens 2 in FIG. 6 or the contact lens 2 in FIG. 6 that is provided with the communication electrode 20 in FIG. 8 and FIG. 9 is worn on the eyeball. FIG. 24 illustrates an example of a manner in which the contact lens 3 in FIG. 7 or the contact lens 3 in FIG. 7 that is provided with the communication electrode 20 in FIG. 8 and FIG. 9 is worn on the eyeball. FIG. 25 illustrates an example of a cross-sectional configuration of any of the contact lenses 1 to 3 in FIG. 18 to FIG. 24.

In the above-described respective embodiments and modification examples thereof, any of the contact lenses 1 to 3 may further include a shield layer 60 that prevents any entry of external electric field or magnetic field. In the present modification example, for example, as illustrated in FIG. 18 to FIG. 20, the shield layer 60 is mainly provided in a region facing the pupil 110 when the lens section 10 is worn on the eyeball 100. In the present modification example, for example, as illustrated in FIG. 21 to FIG. 25, the shield layer 60 is provided in the region facing the pupil 110 when the lens section 10 is worn on the eyeball 100, and in a region other than the region facing the pupil 110 when the lens section 10 is worn on the eyeball 100. For example, as illustrated in FIG. 21 to FIG. 25, the shield layer 60 is provided at a position that faces the sensor device 30, the controller 40, and the communication electrodes 20 and 50, and that is located on the opposite side of the eyeball 100 in a positional relationship with the sensor device 30, the controller 40, and the communication electrodes 20 and 50. The shield layer 60 is provided, for example, inside the lens section 10. The shield layer 60 includes a conductive material. In the shield layer 60, a portion facing the communication electrode 20 includes, for example, a conductive carbon or a metal, and a portion facing the communication electrode 50 includes, for example, a transparent conductive material, such as ITO, ITiO, IZO, or carbon nanotube. It is to be noted that the whole shield layer 60 may include a conductive carbon or a metal. As an alternative, the whole shield layer 60 may include a transparent conductive material, such as ITO, ITiO, IZO, or carbon nanotube.

In the present modification example, the shield layer 60 is provided. This allows the sensor device 30, the controller 40, and the communication electrodes 20 and 50 to reduce an adverse influence exerted by the external electric field or magnetic field. This makes it possible to perform high-accuracy measurement by the use of the sensor device 30. Further, in a case where the communication electrodes 20 and 50 include a metal material, providing the shield layer 60 makes it possible to prevent observation of flare due to reflection or iridescence due to diffraction on the communication electrodes 20 and 50.

Modification Example D

FIG. 26 illustrates an example of functional blocks of any of the contact lenses 1 to 3 according to the above-described modification examples B and C. In any of the contact lenses 1 to 3 according to the above-described modification examples B and C, the controller 40 may include, for example, a signal generating section 41, a noise reduction section 42, and an arithmetic section 43. The signal generating section 41 generates a signal corresponding to information (a detection signal) acquired by the sensor device 30, and outputs the generated signal to an external apparatus through the communication electrodes 20 and 50. The noise reduction section 42 acquires a signal from the external apparatus through the communication electrodes 20 and 50. Further, the noise reduction section 42 uses a noise signal acquired by the shield layer 60 to reduce any noise included in the signal acquired from the external apparatus through the communication electrodes 20 and 50, and outputs a signal (a noise reduction signal) obtained by such noise reduction operation to the arithmetic section 43. The arithmetic section 43 performs arithmetic operation based on the noise reduction signal inputted from the noise reduction section 42.

In the present modification example, any noise included in the signal acquired from the external apparatus through the communication electrodes 20 and 50 is reduced using the noise signal acquired by the shield layer 60. Therefore, even in a case where any noise caused by external electric field or magnetic field is superimposed on a signal acquired by the communication electrodes 20 and 50, the use of the noise signal acquired by the shield layer 60 makes it possible to reduce such noise. As a result, this allows high-speed communication to be performed.

Modification Example E

FIG. 27 illustrates an example of the shield layer 60 included in any of the contact lenses 1 to 3 according to the above-described modification examples B, C, and D. In any of the contact lenses 1 to 3 according to the above-described modification examples B, C, and D, the communication electrodes 20 and 50 each include a plurality of wiring lines adjacent to each other with a predetermined gap in between. At this time, the plurality of wiring lines configuring the communication electrode 20 has the narrowed portion 21 in which a gap narrows locally. The plurality of wiring lines configuring the communication electrode 50 has the narrowed portion 51 in which a gap narrows locally. For example, as illustrated in FIG. 27, the shield layer 60 has an opening 61 at a position facing the narrowed portion 51. This allows an electric field generated in the narrowed portion 51 to be outputted to an outside through the opening 61. Further, this makes it possible to receive an external electric field in the narrowed portion 51 (the communication electrode 20) through the opening 61. As a result, it is possible to perform communication between any of the contact lenses 1 to 3 and an external apparatus with a space quite close to a human body in between.

Modification Example F

FIG. 28 illustrates an example of functional blocks of any of the contact lenses 1 to 3 according to the above-described respective embodiments and modification example A. In any of the contact lenses 1 to 3 according to the above-described respective embodiments and modification example A, the controller 40 may include, for example, a signal generating section 41, a noise reduction section 42, and an arithmetic section 43. The signal generating section 41 generates a signal corresponding to information (a detection signal) acquired by the sensor device 30, and outputs the generated signal to an external apparatus through the communication electrodes 20 and 50. The noise reduction section 42 acquires a signal from the external apparatus through the communication electrodes 20 and 50. For example, the noise reduction section 42 reduces any noise included in a data signal on the basis of a signal (a noise signal A) acquired through the communication electrodes 20 and 50 during a period of time when no communication is performed with the external apparatus, and a signal (a data signal B) acquired from the external apparatus through the communication electrodes 20 and 50 during a period of time when communication is performed with the external apparatus. The noise reduction section 42 reduces any noise included in the data signal B, for example, by removing the noise signal A from the data signal B. For example, the noise reduction section 42 outputs a signal (a noise reduction signal) obtained by reducing the noise included in the data signal B to the arithmetic section 43. The arithmetic section 43 performs arithmetic operation based on the noise reduction signal inputted from the noise reduction section 42.

In the present modification example, the noise included in the data signal B acquired from the external apparatus through the communication electrodes 20 and 50 is reduced using the noise signal A acquired through the communication electrodes 20 and 50. Therefore, even in a case where any noise caused by external electric field or magnetic field is superimposed on a signal acquired by the communication electrodes 20 and 50, it is possible to reduce the noise included in the data signal B. As a result, this allows high-speed communication to be performed.

In the present modification example, any noise included in a detection signal obtained from the sensor device 30 may be reduced. On the basis of, for example, a detection signal (a noise signal C) obtained from the sensor device 30 during a period of time when the sensor device 30 does not function as a sensor, and a detection signal (a data signal D) acquired from the sensor device 30 during a period of time when the sensor device 30 functions as a sensor, the signal generating section 41 reduces any noise included in the data signal D. The signal generating section 41 reduces the noise included in the data signal D, for example, by removing the noise signal C from the data signal D. For example, the signal generating section 41 outputs a signal obtained by reducing the noise included in the data signal D to the external apparatus through the communication electrodes 20 and 50.

In the present modification example, the noise included in the detection signal (the data signal D) acquired from the sensor device 30 during a period of time when the sensor device 30 functions as a sensor is reduced using the detection signal (the noise signal C) obtained from the sensor device 30 during a period of time when the sensor device 30 does not function as a sensor. Therefore, even in a case where any noise caused by external electric field or magnetic field is superimposed on the detection signal obtained from the sensor device 30, it is possible to reduce the noise included in the data signal D. As a result, this allows high-speed communication to be performed.

7. Fourth Embodiment

[Configuration]

Next, description is provided on a communication system 4 according to a fourth embodiment of the present disclosure. Each of FIG. 29 and FIG. 30 illustrates an example of a schematic configuration of the communication system 4 that performs communication between any of the contact lenses 1 to 3 according to the above-described respective embodiments and modification examples thereof and a wearable apparatus 5. The communication system 4 includes any of the contact lenses 1 to 3 according to the above-described respective embodiments and modification examples thereof and the wearable apparatus 5.

FIG. 29 exemplifies any of the contact lenses 1 to 3 that are each not provided with the shield layer 60. FIG. 30 exemplifies any of the contact lenses 1 to 3 that are each provided with the shield layer 60 that covers the sensor device 30, the controller 40, and the communication electrode 20, the communication electrode 50, or a combination of the communication electrodes 20 and 50. It is to be noted that, in FIG. 30, the shield layer 60 may not cover the communication electrode 20, the communication electrode 50, or the combination of the communication electrodes 20 and 50. Each of the communication electrode 20, the communication electrode 50, or the combination of the communication electrodes 20 and 50 corresponds to a specific example of a "first communication electrode" of the present disclosure.

The wearable apparatus 5 is a wearable apparatus of a wristband type or a wristwatch type. The wearable apparatus 5 includes, for example, a communication electrode 54 that receives a signal outputted from any of the contact lenses 1 to 3, a chassis 52 that houses the communication electrode 54, and a wrist fixing belt 53 that supports the chassis 52. The communication electrode 54 corresponds to a specific example of a "second communication electrode" of the present disclosure.

In the present embodiment, the communication electrode 20, the communication electrode 50, or the combination of the communication electrodes 20 and 50 is provided in a portion of the lens section 10. This makes it possible to reduce deterioration in the visibility resulting from the communication electrode 20, the communication electrode 50, or the combination of the communication electrodes 20 and 50, as compared with a case where a plate-like communication electrode is provided. Further, the ability of reducing deterioration in the visibility resulting from the communication electrode 20, the communication electrode 50, or the combination of the communication electrodes 20 and 50 allows the communication electrode 20 to be provided also in the middle of the lens section 10, or the communication electrode 50 to be provided at the periphery thereof. This makes it possible to have a wider region allowing for formation of the communication electrode 20, the communication electrode 50, or the combination of the communication electrodes 20 and 50, which makes it possible to ensure a capacity or a length of the communication electrode 20, the communication electrode 50, or the combination of the communication electrodes 20 and 50. As a result, this allows for improvement in the communication sensitivity and the communication speed.

It is to be noted that the effects described in the present specification are merely examples. The effects of the present disclosure are not limited to the effects described herein. The present disclosure may have any effects other than the effects described herein.

Further, for example, the present disclosure may be configured as follows.

(1)

A contact lens including:

a lens section to be worn on an eyeball;

a communication electrode that is provided in the lens section;

a sensor device that is provided in the lens section;

a controller that is provided in the lens section, and supplies electric power to the communication electrode, while outputting a signal corresponding to information acquired by the sensor device to the communication electrode; and a shield layer that is provided in the lens section, and is provided at a position facing at least one of the sensor device, the controller, or the communication electrode.

(2)

The contact lens according to (1), in which the shield layer is provided mainly in a region facing a pupil when the lens section is worn on the eyeball, and includes a transparent conductive material.

(3)

The contact lens according to (2), in which the communication electrode is provided mainly in a region facing the pupil when the lens section is worn on the eyeball, and includes a transparent conductive wiring line, a wiring line that includes a low-reflectance material, or a wiring line in which at least one surface of a top surface, a side surface, or a bottom surface of a layer including a high-reflectance material is covered with a layer including a low-reflectance material.

(4)

The contact lens according to (1), in which the shield layer is provided mainly in a region other than a region facing a pupil when the lens section is worn on the eyeball, and includes a conductive carbon or a metal.

(5)

The contact lens according to (4), in which the communication electrode is provided mainly in a region other than the region facing the pupil when the lens section is worn on the eyeball, and includes a conductive carbon wiring line or a metal wiring line.

(6)

The contact lens according to (1), in which the communication electrode includes a first partial electrode that is provided mainly in a region facing a pupil when the lens section is worn on the eyeball, and a second partial electrode that is provided mainly in a region other than the region facing the pupil when the lens section is worn on the eyeball, and in the shield layer, a portion facing the first partial electrode includes a transparent conductive material, and a portion facing the second partial electrode includes a conductive carbon or a metal.

(7)

The contact lens according to (6), in which the first partial electrode includes a transparent conductive wiring line, a wiring line that includes a low-reflectance material, or a wiring line in which at least one surface of a top surface, a side surface, or a bottom surface of a layer including a high-reflectance material is covered with a layer including a low-reflectance material, and the second partial electrode includes a conductive carbon wiring line or a metal wiring line.

(8)

The contact lens according to any one of (1) to (7), in which the controller uses a noise signal acquired by the shield layer to reduce noise included in a signal acquired from an external apparatus through the communication electrode.

(9)

The contact lens according to any one of (1) to (8), in which the communication electrode includes a plurality of wiring lines adjacent to each other with a predetermined gap in between, the plurality of wiring lines has a narrowed portion in which the gap narrows locally, and the shield layer is provided in a region facing the communication electrode, and has an opening at a position facing the narrowed portion.

(10)

A communication system provided with a contact lens and a wearable apparatus, the contact lens including:

a lens section to be worn on an eyeball;

a communication electrode that is provided in the lens section;

a sensor device that is provided in the lens section;

a controller that is provided in the lens section, and supplies electric power to the communication electrode, while outputting a signal corresponding to information acquired by the sensor device to the communication electrode; and a shield layer that is provided in the lens section, and is provided at a position facing at least one of the sensor device, the controller, or the communication electrode.

According to the contact lens and the communication system of the respective embodiments of the present disclosure, the use of the shield layer reduces an adverse influence exerted by external electric field and magnetic field, which makes it possible to perform high-accuracy measurement by the use of the sensor device. This allows for providing the contact lens and the communication system that exhibit enhanced noise tolerance. It is to be noted that the effects of the present disclosure are not necessarily limited to the effects described herein, and any of the effects described in the present specification may be provided.

This application claims the priority on the basis of Japanese Patent Application No. 2017-245990 filed on Dec. 22, 2017 with Japan Patent Office, the entire contents of which are incorporated in this application by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. A contact lens comprising:

a lens section to be worn on an eyeball;

a communication electrode that is provided in the lens section;

a sensor device that is provided in the lens section;

a controller that is provided in the lens section, and supplies electric power to the communication electrode, while outputting a signal corresponding to information acquired by the sensor device to the communication electrode; and a shield layer that is provided in the lens section, and is provided at a position facing at least one of the sensor device, the controller, or the communication electrode.

2. The contact lens according to claim 1, wherein the shield layer is provided mainly in a region facing a pupil when the lens section is worn on the eyeball, and includes a transparent conductive material.

3. The contact lens according to claim 2, wherein the communication electrode is provided mainly in a region facing the pupil when the lens section is worn on the eyeball, and includes a transparent conductive wiring line, a wiring line that includes a low-reflectance material, or a wiring line in which at least one surface of a top surface, a side surface, or a bottom surface of a layer including a high-reflectance material is covered with a layer including a low-reflectance material.

4. The contact lens according to claim 1, wherein the shield layer is provided mainly in a region other than a region facing a pupil when the lens section is worn on the eyeball, and includes a conductive carbon or a metal.

5. The contact lens according to claim 4, wherein the communication electrode is provided mainly in a region other than the region facing the pupil when the lens section is worn on the eyeball, and includes a conductive carbon wiring line or a metal wiring line.

6. The contact lens according to claim 1, wherein
the communication electrode comprises a first partial electrode that is provided mainly in a region facing a pupil when the lens section is worn on the eyeball, and a second partial electrode that is provided mainly in a region other than the region facing the pupil when the lens section is worn on the eyeball, and
in the shield layer,
a portion facing the first partial electrode includes a transparent conductive material, and
a portion facing the second partial electrode includes a conductive carbon or a metal.

7. The contact lens according to claim 6, wherein
the first partial electrode includes a transparent conductive wiring line, a wiring line that includes a low-reflectance material, or a wiring line in which at least one surface of a top surface, a side surface, or a bottom surface of a layer including a high-reflectance material is covered with a layer including a low-reflectance material, and
the second partial electrode includes a conductive carbon wiring line or a metal wiring line.

8. The contact lens according to claim 1, wherein the controller uses a noise signal acquired by the shield layer to reduce noise included in a signal acquired from an external apparatus through the communication electrode.

9. The contact lens according to claim 1, wherein
the communication electrode includes a plurality of wiring lines adjacent to each other with a predetermined gap in between,
the plurality of wiring lines has a narrowed portion in which the gap narrows locally, and
the shield layer is provided in a region facing the communication electrode, and has an opening at a position facing the narrowed portion.

10. A communication system provided with a contact lens and a wearable apparatus, the contact lens comprising:
a lens section to be worn on an eyeball;
a communication electrode that is provided in the lens section;
a sensor device that is provided in the lens section;
a controller that is provided in the lens section, and supplies electric power to the communication electrode, while outputting a signal corresponding to information acquired by the sensor device to the communication electrode; and
a shield layer that is provided in the lens section, and is provided at a position facing at least one of the sensor device, the controller, or the communication electrode.

11. The communication system according to claim 10, wherein the controller uses a noise signal acquired by the shield layer to reduce noise included in a signal acquired from an external apparatus through the communication electrode.

12. The communication system according to claim 10, wherein the shield layer is provided mainly in a region facing a pupil when the lens section is worn on the eyeball, and includes a transparent conductive material, and wherein the communication electrode is provided mainly in a region facing the pupil when the lens section is worn on the eyeball, and includes a transparent conductive wiring line, a wiring line that includes a low-reflectance material, or a wiring line in which at least one surface of a top surface, a side surface, or a bottom surface of a layer including a high-reflectance material is covered with a layer including a low-reflectance material.

13. The communication system according to claim 10, wherein
the communication electrode comprises a first partial electrode that is provided mainly in a region facing a pupil when the lens section is worn on the eyeball, and a second partial electrode that is provided mainly in a region other than the region facing the pupil when the lens section is worn on the eyeball, and
in the shield layer,
a portion facing the first partial electrode includes a transparent conductive material, and
a portion facing the second partial electrode includes a conductive carbon or a metal.

14. The communication system according to claim 10, wherein
the communication electrode includes a plurality of wiring lines adjacent to each other with a predetermined gap in between,
the plurality of wiring lines has a narrowed portion in which the gap narrows locally, and
the shield layer is provided in a region facing the communication electrode, and has an opening at a position facing the narrowed portion.

* * * * *